United States Patent [19]
Yoshioka et al.

[11] Patent Number: 4,933,439
[45] Date of Patent: Jun. 12, 1990

[54] TYLOSIN DERIVATIVES AND PROCESSES FOR PRODUCING THE SAME

[75] Inventors: Takeo Yoshioka, Ayase; Azuma Watanabe, Fujisawa; Hiroyuki Chiba, Yokohama; Kaichiro Kominato, Yamato; Kohki Kiyoshima, Fujisawa; Yasuo Fukagawa, Kamakura; Hiroshi Tone, Yokohama; Rokuro Okamoto, Fujisawa, all of Japan

[73] Assignee: Sanraku Incorporated, Tokyo, Japan

[21] Appl. No.: 272,601

[22] Filed: Nov. 17, 1988

[30] Foreign Application Priority Data

Jun. 21, 1988 [JP] Japan .................. 63-153886
Aug. 8, 1988 [JP] Japan .................. 63-198349

[51] Int. Cl.$^5$ .......................... C07M 17/08
[52] U.S. Cl. ...................... 536/7.1; 536/124
[58] Field of Search .................. 536/7.1, 124

[56] References Cited
U.S. PATENT DOCUMENTS
4,242,504 12/1980 Sakakibara et al. .......... 536/7.1

Primary Examiner—Johnnie R. Brown
Assistant Examiner—Elli Peselev
Attorney, Agent, or Firm—Jordan and Hamburg

[57] ABSTRACT

Tylosin derivatives represented by the following general formula (I):

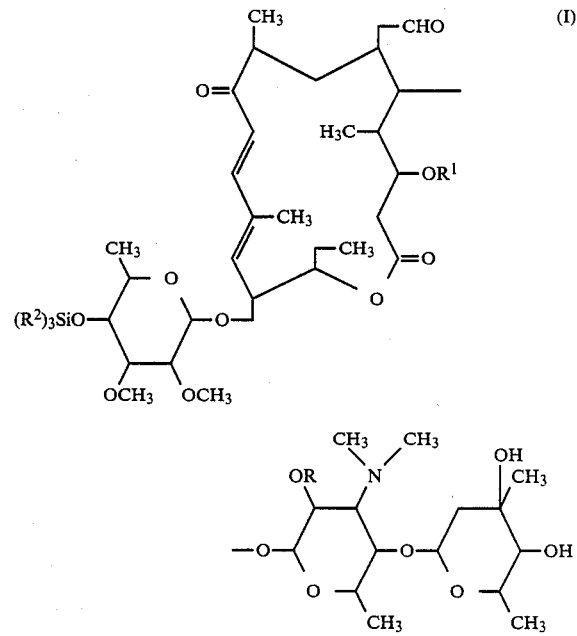

[wherein R denotes a hydrogen atom, acetyl, propionyl or a radical of $Si(R^2)_3$ (in which $R^2$ is a lower alkyl group), and $R^1$ stands for a hydrogen atom or a radical of $Si(R^2{}_3)$] are useful as intermediates for the synthesis of 4″-acyl derivatives of tylosin because, after introduction of any desired acyl group at the 4″-hydroxyl group, the silyl protective group can be readily removed without liberation of the acyl group. This invention also provides processes for producing the tylosin derivatives. More specifically, it provides a melthod of selectively protecting 2′- and 4‴-hydroxyl groups of tylosin (those of higher reactivity among the hydroxyl groups involved); a method of selectively protecting only the 4‴-hydroxyl group of tylosin; a method of selectively protecting the 3- and 4‴-hydroxyl groups of 2′-O-acyl-tylosin; and a method of protecting 3-, 2′- and 4‴-hydroxyl groups of tylosin.

7 Claims, No Drawings

TYLOSIN DERIVATIVES AND PROCESSES FOR PRODUCING THE SAME

BACKGROUND OF THE INVENTION

1. Field of the Invention

This invention relates to 2', 4'''-O-di-O-trialkylsilyl derivatives of tylosin, 3,2',4'''-tri-O-trialkylsilyl derivatives of tylosin, 4'''-O-trialkylsilyl derivatives of tylosin, 3,4'''-di-O-trialkylsilyl derivatives of 2'-O-acyl-tylosins and 4'''-O-trialkylsilyl derivatives of 2'-O-acyl-tylosins, which are useful as intermediates for the synthesis of various tylosin derivatives (components of 16-membered macrolide antibiotics); and to processes for producing the same.

2. Description of the Prior Art

16-Membered macrolide antibiotics have excellent anti-bacterial activity and are widely used as medicines (for both humans and animals) and additives to animal feeds. Tylosin, in particular, is being produced in large quantities on a commercial scale.

However, macrolide antibiotics generally have the disadvantage of inefficient absorption and excretion when administered to living bodies. In addition, drug-resistant strains of bacteria have appeared as is usual with antibiotics in general. Under the circumstances, many chemical and biological studies are under way on the development of new tylosin derivatives having improved absorption and excretion characteristics and imparted with antibacterial potency against the drug-resistant strains.

Tylosin is a compound represented by the following formula:

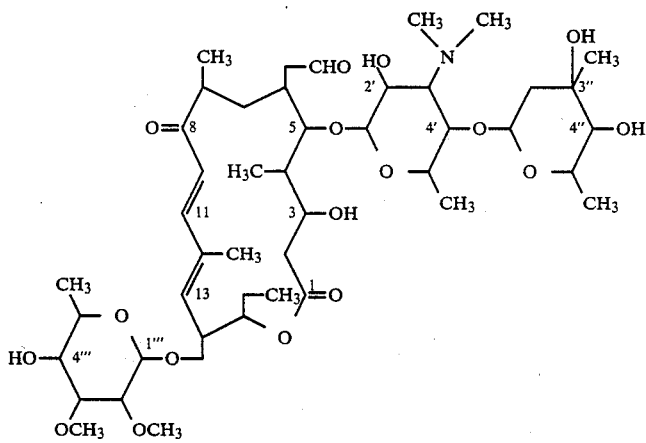

It has been found that derivatives thereof in which the hydroxyl group at 4''-position of the disaccharide residue attached to the 5-position of tylosin has been acylated [for example, 4''-O-(4-methoxyphenylacetyl)-tylosin, 4''-O-(4-acetylphenylacetyl)tylosin, 4''-O-(4-methylthiophenylacetyl)tylosin, 4''-O-(3-pyridylacetyl)tylosin and 4''-O-(4-methylsulfonyl-phenylacetyl)tylosin]have high antibacterial activity against the bacteria resistant to macrolide antibiotics and show improved absorption and excretion efficiency (U.S. Pat. Nos. 4612372 and 4205163).

For the chemical synthesis of these 4''-O-acyl derivatives from tylosin, a method has been adopted in which the two hydroxyl groups at 2'-and 4'''-positions are previously protected, a desired acyl group is introduced to 4''-position, and the two protective groups are removed [M. Tsuchiya et al.: J. Antibiotics, 35, 661 (1982)].

For example, tylosin is allowed to react with acetic anhydride to form 2'-0-acetyltylosin, which is acylated in dichloromethane in the presence of pyridine by a halogenated lower-alkanoyl halide, a lower-alkoxycarbonyl halide or a phenoxyacetyl halide, the corresponding 2',4'''-di-O-acyltylosin thus formed is isolated, and a desired acyl group is introduced into the 4''-position, followed by removal of the protective group (or groups) at the 4'''-and/or 2'-positions (U.S. Pat. No. 4205163). This method, however, gives 4''-O-acyl derivatives in a low yield of 10 to 30% and requires chromatography for isolation.

On the other hand, a technique has been disclosed in which 4'''-O-tert-butyldimethylsilyltylosin is prepared by treating tylosin with tertbutyldimethylchlorosilane in dimethylformamide in the presence of imidazole (U.S. Pat. No.393901).

Tylosin contains four secondary hydroxyl groups in the molecule, and the ease of acylation is in the order of 2'-, 4'''-, 4''-and 3-positions. Hence, the hydroxyl groups at 2'- and 4'''-positions must be protected when tylosin derivatives (particularly 4''-O-acyltylosin) are chemically synthesized by the above-mentioned conventional methods. The 2'hydroxyl group can be easily differentiated from the other hydroxyl groups because it can be acylated in the absence of basic catalyst due to the effect of the adjacent dimethylamino group at the 3'position. However, the succeeding acylation of 4'''-hydroxyl group for protection gives, as by-product, 2'-O-acyl protected-4'', 4'''-di-O-acylprotected-tylosin because of little difference in reactivity between the 4'''- and 4''- hydroxyl groups, and hence this by-product must be removed by chromatography or the like in order to obtain pure 2'-O-acyl-protected-4'''-O-acyl-protected-tylosin. In addition, the following acylation of 4''-hydroxyl group is accompanied by acylation of the 3-hydroxyl group. Thus, the final desired product (4''-O-acyltylosin derivatives) is obtained only in a low yield.

On the other hand, selective protection of the 4'''-hydroxyl group with tert-butyldimethylsilyl group also involves several problems: the reaction requires a large excess of relatively expensive reagents, tertbutyldimethylchlorosilane and imidazole; the objective 4'''-O-tert-butyldimethylsilyl derivative has to be isolated by chromatography or other techniques because of its rather low yield; and the reaction takes a long time for completion.

SUMMARY OF THE INVENTION

The object of this invention is to provide a method of selectively protecting 2'- and 4'''-hydroxyl groups of tylosin (those of higher reactivity among the hydroxyl groups in the molecule); to provide new tylosin derivatives in which the 2'- and 4'''-hydroxyl groups are protected; to provide a method of selectively protecting only the 4'''-hydroxyl group of tylosin; to provide new tylosin derivatives in which the 4'''hydroxyl group is protected; to provide a method of selectively protecting the 3- and 4'''-hydroxyl groups of 2'-O-acyltylosin; to provide new 2'-O-acyltylosin derivatives in which the 3-and 4'''-hydroxyl groups are protected; to provide a method of selectively protecting 3-, 2'- and 4'''-hydroxyl groups of tylosin; and to provide new tylosin derivatives in which 3-, 2'- and 4'''hydroxyl groups are protected.

Thus, this invention relates to tylosin derivatives represented by the following general formula (I):

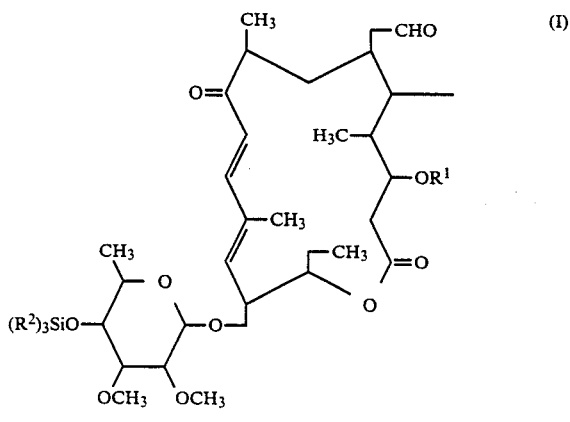

wherein R denotes a hydrogen atom, acetyl, propionyl or a radical of $Si(R^2)_3$ (in which $R^2$ is a lower alkyl group), and $R^1$ stands for a hydrogen atom or a radical of $Si(R^2)_3$.

The tylosin derivatives of this type are novel compounds, and are useful as intermediates for the synthesis of 4''-acyl derivatives of tylosin because, after introduction of any desired acyl group at the 4''-hydroxyl group, the silyl protective group can be readily removed without liberation of the acyl group.

DETAILED DESCRIPTION OF THE INVENTION

Of the compounds of formula (I), those in which R is $Si(R^2)_3$ and $R^1$ is a hydrogen atom are represented by the following formula (II):

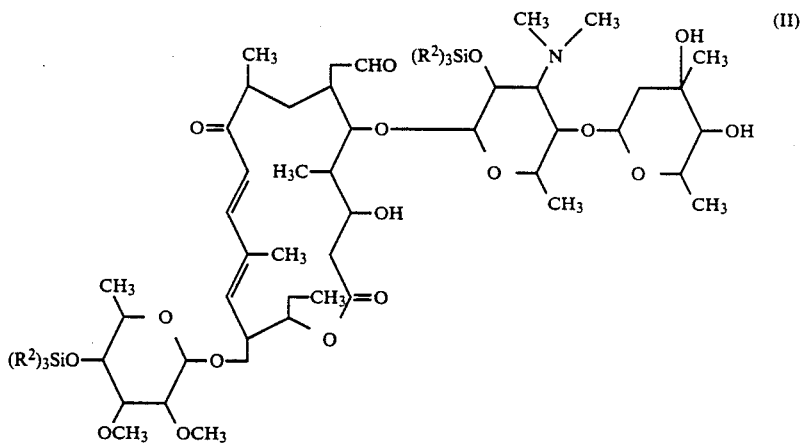

wherein $R^2$ is a linear or branched, lower alkyl group of 1 to 4 carbon atoms, such as methyl, ethyl, n-propyl, isopropyl, n-butyl, isobutyl and tert butyl. Of these, methyl, ethyl and propyl are the most preferred, and either the same or different alkyl groups may be attached to the silicon atom.

Illustrative examples of tylosin derivatives of formula (II) include 2', 4'''-di-O-trimethylsilyltylosin, 2',4'''-di-O-triethylsilyltylosin, 2',4'''-di-O-tripropylsilyltylosin, 2',4'''di-O- tributylsilyltylosin and 2',4'''-di -O-tri-tert-butylsilyltylosin.

The compounds of formula (II) can be prepared by trialkylsilylation of tylosin in an inert solvent.

The starting material tylosin is a known compound having the structure as shown earlier, which is obtainable from a culture solution of Streptomyces fradiae NRRL 2702 (refer to U.S. Pat. No. 3,178,341). It is dissolved or suspended in an inert solvent and allowed to react with a silylating reagent. The inert solvent may be any solvent that causes substantially no adverse effect to the silylating reaction. Illustrative of such solvents are benzene, toluene, dichloromethane, dichloroethane, chloroform, diethyl ether, tetrahydrofuran, 1,4-dioxane, ethyl acetate, butyl acetate and dimethylformamide, which may be used either alone or in combination.

As examples of the silylating reagent, there may be mentioned trimethylchlorosilane, trimethylbromosilane, triethylchlorosilane, tripropylchlorosilane, tributylchlorosilane, tri-tertbutylchlorosilane, hexamethyldisilazane, bistrimethylsilylurea, trimethylsilylimidazole, N-trimethylsilyldialkylamine, bis- and monosilylacetamide, and mixtures thereof.

The reaction is carried out at $-50°$ to $50°$ C., preferably at $-30°$ to $25°$ C., for 0.5 to 25 hours with stirring.

The amount of silylating reagent to be used is 2 to 3 moles, preferably 2.1 to 2.5 moles, per mole of tylosin, and an organic base, such as triethylamine, diisopropylethylamine, cyclohexyldiethylamine, imidazole, pyridine and collidines, may also be used as reaction auxiliary.

The product formed can be isolated from the reaction mixture by using techniques commonly employed in this field, such as extraction with an organic solvent and purification by silica gel column chromatography. However, the reaction mixture may be submitted to the successive step without further treatment when the product is used for the synthesis of an intermediate.

Of the compounds of formula (I), those in which R is a hydrogen atom, acetyl or propionyl group and $R^1$ is a hydrogen atom are represented by the following formula (III):

The starting materials, 2'-O-acyltylosins (e.g., 2'-O-acetyltylosin and 2'-O-propionyltylosin), are known compounds disclosed in Japanese Patent Publication No. 22649 (1979) and in Antibiotics and Chemotherapy, 11, 328–54 (1961).

Tylosin or a 2'-O-acyltylosin is dissolved in an alkyl acetate, such as methyl acetate, ethyl acetate, propyl acetate and butyl acetate (of which ethyl acetate is the most preferred), and allowed to react with a silylating reagent, such as trimethylchlorosilane, trimethylbromosilane, triethylchlorosilane and tripropylchlorosilane.

The reaction is carried out at $-50°$ to $50°$ C., preferably at $-30°$ to $25°$ C., for 0.5 to 20 hours with stirring.

The amount of silylating reagent to be used is 1.2 to 3.0 moles, preferably 1.5 to 2.0 moles, per mole of tylosin or 2'-O-acetyltylosin, and an organic base, such as triethylamine and diisopropylethylamine, may also be used as reaction auxiliary.

The product of formula (III) formed can be isolated by washing and filtering the reaction mixture and distilling off the solvent from the filtrate.

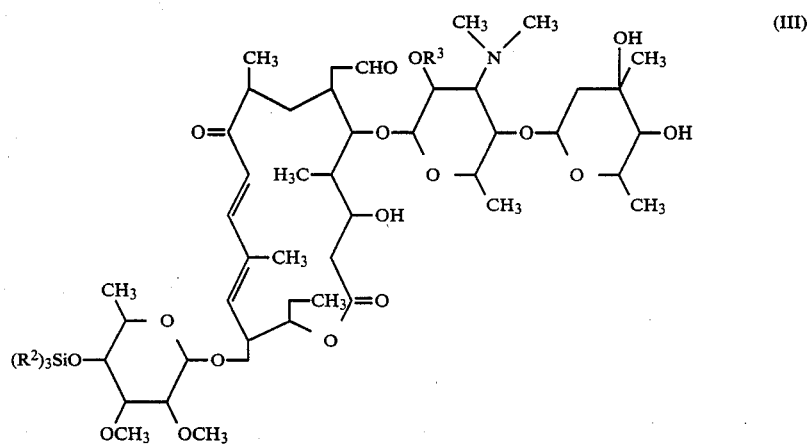

(III)

wherein $R^3$ is a hydrogen atom, acetyl or propionyl group, and $R^2$ is a lower alkyl group. Illustrative examples of tylosin derivatives of formula (III) include 4'''-O-trimethylsilyltylosin, 4'''-O-triethylsilyltylosin, 2'-O-acetyl-4'''-O-trimethylsilyltylosin, 2'-O-propionyl-4'''-O-trimethylsilyltylosin and 4'''-O-tripropylsilyltylosin.

The compounds of formula (III) can be selectively prepared in high yields by trialkylsilylation of tylosin or a 2'-O-acyltylosin in an alkyl acetate.

In this reaction, the silylating reagent selectively reacts with the 4'''-hydroxyl group of tylosin and does not react with the 4''-hydroxyl group by reacting tylosin and 2'-O-acyltylosin with trialkylsilylating reagent, wherein alkylester acetic acid is used as solvent.

Of the compounds of formula (I), those in which R is acetyl, propionyl or a radical of $Si(R^2)_3$ and $R^1$ is a radical of $Si(R^2)_3$ are represented by the following formula (IV):

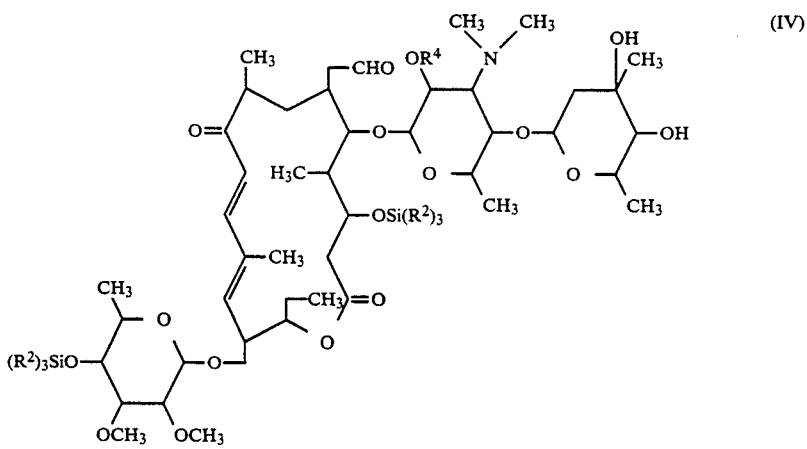

wherein R⁴ is acetyl, propionyl or a radical of Si(R²)₃, and R² is as defined above. Illustrative examples include 2'-O-acetyl-3,4'''-di-O-trimethylsilyltylosin, 2'-O-propionyl-3,4'''-di-O-trimethylsilyltylosin, 2'-O-acetyl-3,4'''-di-O-triethylsilyltylosin, 2'-O-propionyl- 3,4'''-di-O-triethylsilyltylosin, 2'-O-acetyl-3,4'''-di-O-tripropylsilyltylosin, 3,2',4'''-tri-O-trimethylsilyltylsin, 3,2',4'''-tri-O-triethylsilyltylosin and 3,2',4'''-tri-O-tripropylsilytylosin.

The compounds of formula (IV) can be obtained by dissolving a 2'-O-acyltylosin (e.g., 2'-O-acetyltylosin or 2'-O-propionyltylosin) in a solvent, adding a boric acid derivative to the solution, and reacting the resulting mixture with a silylating reagent (e.g., trimethylchlorosilane, trimethylbromosilane, triethylchlorosilane and tripropylchlorosilane).

As examples of the solvent, there may be mentioned aromatic hydrocarbons, halogenated hydrocarbons, ethers, esters, dimethylformamide, dimethyl sulfoxide, acetonitrile, a mixture of toluene and dimethyl sulfoxide, and a mixture of ethyl acetate and dimethylformamide.

As the boric acid derivative, may be used boric acid, boric anhydride, phenylboric acid or a triester of boric acid. The boric acid derivative may be added as solid or in the form of a solution in a solvent as mentioned above. The suitable amount is 0.5 to 1.2 moles, preferably 0.8 to 1.0 mole, per mole of tylosin or 2'-acetyltylosin. It is added at 0 to 50° C., preferably at room temperature, while stirring, and the reaction is continued for 0.5 to 3 hours, preferably one hour, to protect the 4''- and 3''-hydroxyl groups. The reaction mixture is dehydrated as required, and a silylating reagent and an organic base are added to effect silylation at 3 and 4'''-positions or at 3-, 2'and 4'''-positions.

The amount of silylating reagent to be used is 3 to 8 molar proportions, preferably 4 to 5 molar proportions, for 2'-O-acyltylosin, and 4 to 10 molar proportions, preferably 5 to 7 molar proportions, for tylosin. It may be added all at once or in several parts. The organic base (e.g., triethylamine or diisopropylethylamine) is used in an amount of 1.0 to 2.0 times, preferably 1.1 to 1.2 times, the mole of silylating reagent.

The product of formula (IV) thus formed can be isolated by diluting the reaction mixture with an organic solvent (e.g., toluene, ethyl acetate and chloroform), washing the diluted solution with saturated aqueous solution of sodium bicarbonate and aqueous solution of sodium chloride in that order, followed by drying over anhydrous sodium sulfate, and distilling off the solvent from the dried solution.

The new tylosin derivatives of this invention represented by the general formula (I), in which the highly reactive 2'- and 4'''-hydroxyl groups of tylosin have been selectively protected, are useful intermediates to which a desired acyl group can be efficiently introduced at the 4''-position —the desired acyl group can be introduced by reaction with a reactive derivative of the corresponding organic acid, and the silyl groups at the 2'-4'''and 3-positions can be readily released by, for example, hydrolysis under mild conditions.

The following Examples will further illustrate the invention but are not intended to limit its scope.

EXAMPLE 1

2',4'''-O-Di-trimethylsilyltylosin

To an ice-cooled solution of 5 g (5.46 mmoles) tylosin in 30 ml anhydrous ethyl acetate, was added 1.83 ml (13.1 mmoles) triethylamine in a nitrogen atmosphere. Trimethylchlorosilane (1.45 ml, 11.5 mmoles) was then added, and the mixture was slowly returned to room temperature and stirred for 24 hours. The reaction mixture was diluted with ethyl acetate, and the diluted solution was washed with saturated aqueous solution of sodium bicarbonate and saturated aqueous solution of sodium chloride in that order, and dried over anhydrous sodium sulfate. After filtering off the drying agent, the filtrate was concentrated to give 5.53 g (95.7%) of 2',4'''-di-O-trimethylsilyltylosin.

$[\alpha]^{24.5}_D$: −43.4°(c 0.997, CHCl₃).

UV: $\lambda^{CH_3OH}_{max}$ 284 nm (ϵ21.000).

IR: $\nu^{CHCl_3}_{max}$ 1710cm⁻¹ (aldehyde, ester), 1670cm⁻¹ (conjugated ketone), 1590cm⁻¹ (double bond).

¹H-NMR (CDCl₃), δ(ppm):
0.15 (9H, s, Si(CH₃)₃), 0.19 (9H, s, Si(CH₃)₃), 1.80 (3H, s, 12-CH₃), 2.49 (6H, s, N(CH₃)₂), 3.51 (3H, s, 2'''-OCH₃), 3.60 (3H, s, 3'''-OCH₃), 4.59 (1H, d, J=8.0 Hz, H-1'''), 5.95 (1H, d, J=10.5 Hz, H-13), 6.28 (1H, d, J=15.5 Hz, H-10), 9.71 (1H, s, CHO)

EXAMPLE 2

4'''-O-Trimethylsilyltylosin

Tylosin (20 g) was dissolved in 150 ml ethyl acetate, 10.1 ml triethylamine was added, and the resulting solution was cooled to −20° C. Trimethylchlorosilane (7.6 ml) was then added dropwise over a period of ten minutes, and the mixture was stirred at that temperature for one hour. The reaction mixture was washed once with 100 ml of saturated aqueous solution of sodium bicarbonate and then twice with 100 ml of saturated aqueous solution of sodium chloride, and dried over anhydrous sodium sulfate. After filtering off the drying agent, the filtrate was concentrated to about 80 ml, and the concentrate was allowed to stand. The crystals which separated out were collected by filtration, washed with 15 ml ethyl acetate and dried under reduced pressure, giving the first crystals of 4'''-O-trimethylsilyltylosin (14.7 g). The second crystals (4.5 g) were obtained by treating the mother liquid in the same way as above. The total yield was 19.2 g.

The physicochemical properties of this compound are as shown below.

$R_f$: 0.42 (CHCl$_3$/MeOH/28%-NH$_4$OH =15:1:0.1).

Melting point: 147°–150° C.

$^1$H-NMR (CDCl3), δ(ppm): (main peaks only) 0.18 (9H, s, Si(CH$_3$)$_3$), 1.80 (3H, s, 12-CH$_3$), 2.49 (6H, s, N(CH$_3$)$_2$), 3.50 (3H, s, 2'''-OCH$_3$), 3.60 (3H, s, 3'''-OCH$_3$), 4.22 (1H, d, J=7.5 Hz, H-1'}, 4.59 (1H, d, J=8.0 Hz, H-1'''), 5.05 (1H, d, H 1''), 5.91 (1H, d, J=10.5 Hz, H-13), 6.24 (1H, d, J=15.5 Hz, H-10), 7.31 (1H, d, J=15.5 Hz, H-11), 9.69 (1H, s, CHO)

EXAMPLE 3

2'-O-Acetyl-4'''-O-trimethylsilyltylosin

2'-O-Acetyltylosin (10 g) was dissolved in 75 ml anhydrous ethyl acetate, 2.7 ml triethylamine was added, and the resulting solution was cooled to −25° C. Trimethylchlorosilane (2.1 ml) was then added dropwise, and the mixture was stirred at that temperature for 18 hours. The reaction mixture was washed once with 50 ml of saturated aqueous solution of sodium bicarbonate and then twice with 50 ml of saturated aqueous solution of sodium chloride, and dried over anhydrous sodium sulfate. After filtering off the drying agent, the filtrate was concentrated to dryness, giving 9.0 g of 2'-O-acetyl-4'''-O-trimethylsilyltylosin. The physicochemical properties of this compound are as shown below.

Rf: 0.54 benzene/acetone =2:1).

$^1$H-NMR (CDCl$_3$), δ(ppm): (main peaks only) 0.18 (9H, s, Si(CH$_3$)$_3$), 1.80 (3H, s, 12-CH$_3$), 2.06 (3H, s, 2'-OCOCH$_3$), 2.39 (6H, s, N(CH$_3$)$_2$, 3.51 (3H, s, 2'''-OCH$_3$), 3.60 (3H, s, 3'''-OCH$_3$), 4.28 (1H, d, J=7.5 Hz, H-1'), 4.60 (1H, d, J=8.0 Hz, H-1'''), 5.05 (1H, d, H-1''), 5.93 (1H, d, J=10.5 Hz, H-13), 6.27 (1H, d, J=15.5 Hz, H-10), 7.32 (1H, d, J=15.5 Hz, H-11), 9.69 (1H, s, CHO).

EXAMPLE 4

2'-O-Acetyl-3,4'''-di-O-trimethylsilyltylosin

2'-O-Acetyltylosin (10.00 g, 10.44 mmoles) was dissolved in 30 ml dimethylformamide in a 100-ml round-bottomed flask fitted with a CaCl$_2$-tube, and the solution was stirred at room temperature while shielding the light. A solution of 516 mg (8.35 mmoles) orthoboric acid, B(OH)$_3$, in 10 ml dimethylformamide was then added in small portions, the resulting solution was stirred at room temperature for two hours, and triethylamine (9.46 ml, 67.8 mmoles) was added dropwise. After five minutes, 7.95 ml (62.62 mmoles) trimethylchlorosilane was added dropwise, and the mixture was stirred at room temperature for 26 hours. The reaction mixture was diluted with an excess amount of toluene, and the diluted solution was washed with saturated aqueous solution of sodium bicarbonate. The aqueous layer was extracted once with toluene, the extract was added to the toluene layer separated above, and the combined solution was washed with saturated aqueous solution of sodium chloride and dried over anhydrous sodium sulfate. Distilling off the solvent from the dried solution under reduced pressure gave 10.92 g of 2'-O-acetyl-3,4'''-di-O-trimethylsilyltylosin.

$[α]^{20}_D$: −64.7° (c 1.0, CHCl$_3$).

IR (CHCl$_3$): 2925, 1740, 1670, 1590 cm$^{-1}$ $^1$H-NMR (CDCl$_3$), δ(ppm): 0.07 (9H, s, Si(CH$_3$)$_3$), 0.16 (9H, s, Si(CH$_3$)$_3$), 1.75 (3H, s, 12-CH$_3$), 2.02 (3H, s, 2'-OCOCH$_3$), 2.35 (6H, s, N(CH$_3$)$_2$), 3.45 (3H, s, 2'''-OCH$_3$), 3.56 (3H, s, 3''-OCH$_3$), 4.56 (1H, d, J=8.0 Hz, H-1'''), 5.85 (1H, d, J=10.0 Hz, H-13), 6.20 (1H, d, J=16.0 Hz, H-10), 7.25 (1H, d, J=16.0 Hz, H-11), 9.70 (1H, s, CHO).

EXAMPLE 5

3,2',4'''-Tri-O-trimethylsilyltylosin

To a solution of 1 g (1.09 mmoles) tylosin in 6 ml ethyl acetate, was added 0.37 ml (2.62 mmoles) triethylamine, the mixture was cooled in ice, 0.14 ml (2.29 mmoles) trimethylchlorosilane was added dropwise, and the resulting solution was stirred at room temperature for 16 hours.

To the reaction mixture, was added slowly 2 ml dimethylformamide solution containing 67.5 mg (1.09 mmoles) boric acid, the mixture was stirred at room temperature for 30 minutes, 0.99 ml (7.01 mmoles) triethylamine and 0.83 ml (6.54 mmoles) trimethylchlorosilane were added dropwise, and stirring was continued for 16 hours. The reaction mixture was poured into saturated aqueous solution of sodium bicarbonate, the resulting mixture was extracted with ethyl acetate, and the extract was washed with saturated aqueous solution of sodium chloride, dried over anhydrous sodium sulfate and concentrated under reduced pressure. The residue was purified by column chromatography on 30 g silica gel [eluents: mixtures of toluene-/acetone (20:1), 10:1), (5:1) and (3:1)], giving 620 mg (50%) of 3,2',4'''-tri-O-trimethylsilyltylosin.

$^1$H-NMR (CDCl$_3$), δ(ppm): 0.07 (9H, s, Si(CH$_3$)$_3$), 0.16 (9H, s, Si(CH$_3$)$_3$), 0.24 (9H, s, Si(CH$_3$)$_3$), 1.78 (3H, s, 12-CH$_3$), 2.50 (6H, s, N(CH$_3$)$_2$), 3.45 (3H, s, 2'''OCH$_3$), 3.60 (3H, s, 3'''-OCH$_3$), 4.58 (1H, d, J=8.0 Hz, H-1'''), 5.90 (1H, d, J=10.0 Hz, H-13), 6.19 (1H, d, J=16.0 Hz, H-10), 7.30 (1H, d, J=16.0 Hz, H 11), 9.73 (1H, s, CHO).

Given below are examples which show that the compounds of this invention are desirable intermediates for synthesizing useful tylosin derivatives through introduction of a desired acyl group to the 4''-position of tylosin.

EXAMPLE 6

Synthesis of 4''-O-(p-methoxyphenylacetyl)tylosin

To an ice-cooled solution of 5 g (5.46 mmoles) tylosin in 30 ml ethyl acetate, was added 1.83 ml (13.1 mmoles) triethylamine in a nitrogen atmosphere, 1.45 ml trimethylchlorosilane was then added dropwise, and the mixture was slowly returned to room temperature and stirred for 24 hours. The reaction mixture was diluted with ethyl acetate, and the diluted solution was washed with saturated aqueous solution of sodium bicarbonate and saturated aqueous solution of sodium chloride in that order, and dried over anhydrous sodium sulfate. After filtering off the drying agent, the filtrate was concentrated to 15 ml, 46.8 mg (0.42 mmoles) dimethylaminopyridine and 5.83 ml (41.8 mmoles) triethylamine were added, and a solution of 3.2792 g (10.43 mmoles) p-methoxyphenylacetic anhydride in 20 ml dichloroethane was added dropwise over a period of ten minutes at −30° C. in a nitrogen atmosphere. The mixture was stirred at that temperature for one hour, 4.24 ml methanol was added, and stirring was continued at 0° C. for 30 minutes. The reaction mixture was treated with lumps of ice (50 ml), saturated aqueous solution of sodium bicarbonate (150 ml) and toluene (200 ml) to effect extraction, the toluene layer was again washed with saturated aqueous solution of sodium bicarbonate and saturated aqueous solution of sodium chloride in that order, and dried over anhydrous sodium sulfate. After filtering off the drying agent, the filtrate was concentrated to dryness, giving 6.59 g of crude 2',4'''-di-O-trimethylsilyl-4''-O-(p-methoxyphenylacetyl)tylosin. It was dissolved in 193.5 ml of a solvent mixture, methanol/water (2:1), and this solution was stirred at 85° C. overnight. Only the methanol was removed by distillation, 25 ml 1,4-dioxane was added, and the resulting mixture was adjusted to pH 2.2 by addition of 2N-HCl and stirred at room temperature for one hour. After adding 450 ml of a buffer solution (pH 2.3), the aqueous layer was washed with toluene, neutralized with 5N-NaOH solution to pH 6.0 and extracted with toluene. The organic layer was washed with saturated aqueous solution of sodium bicarbonate and saturated aqueous solution of sodium chloride in that order and dried over anhydrous sodium sulfate, the drying agent was filtered off, and the filtrate was concentrated to dryness, affording 4.06 g of crude 4''-O-(p-methoxyphenylacetyl)tylosin.

It was again dissolved in 100 ml toluene, the solution was extracted with 650 ml of a buffer solution (pH 2.3), and the aqueous layer was washed with toluene, adjusted to pH 4.0 by addition of 5N NaOH solution and washed with toluene. After adjusting the pH to 6.0 the aqueous solution was extracted with toluene, giving 2.99 g (51.5%) of pure 4''-O-(p-methoxyphenylacetyl)tylosin.

EXAMPLE 7

Synthesis of 4''-O-(p-methoxyphenylacetyl)tylosin through 2'-O-acetyl-3,4'''-di-O-trimethylsilyltylosin To a solution of 0.972 g (0.882 mmole) 2'-O-acetyl-3,4'''-di-O-trimethylsilyltylosin in 3.0 ml ethyl acetate, were added 7.9 mg ($6.5 \times 10^{-2}$ mmole) dimethylaminopyridine and 0.25 ml (1.79 mmoles) triethylamine, and a solution of 359 mg (1.43 mmoles) p-methoxyphenylacetic pivalic anhydride in 3.0 ml ethyl acetate was added dropwise over a period of four minutes under ice cooling in a nitrogen atmosphere. The mixture was stirred at that temperature for three hours, 0.29 ml (7.15 mmoles) methanol was added, and stirring was continued under ice cooling for 30 minutes. The reaction mixture was treated with lumps of ice (10 ml) and extracted with 10 ml ethyl acetate, and the extract was washed with saturated aqueous solution of sodium bicarbonate and saturated aqueous solution of sodium chloride in that order and dried over anhydrous sodium sulfate. After filtering off the drying agent, the filtrate was concentrated, giving 1.05 g (95%) of 2'-O-acetyl-3,441'-di-O-trimethylsilyl-4''-O-(p-methoxyphenylacetyl)tylosin.

1.05 g (0.84 mmoles) of 2'-O-acetyl-3,4'''-di-O-trimethylsilyl-4''-O-(p-methoxyphenylacetyl)tylosin was dissolved in 15.4 ml of a solvent mixture, methanol/water (10:1), and this solution was heated under reflux for 14.5 hours. Only the methanol was distilled off from the reaction mixture, the concentrate was dissolved in 4 ml acetone, and the solution was adjusted to pH 2.2 by addition of 0.15N-HCl and stirred at room temperature for two hours. After washing with toluene and adjusting the pH to 7.6 with 5N-NaOH solution, the aqueous solution was extracted with ethyl acetate, and the extract was washed with a buffer solution (pH 4.3), saturated aqueous solution of sodium bicarbonate and saturated aqueous solution of sodium chloride in that order and dried over anhydrous sodium sulfate. After filtering off the drying agent, the filtrate was concentrated, affording 487 mg (54.5%) of 4''-O-(p-methoxyphenylacetyl)tylosin.

$[\alpha]^{24}_D$: −43.6° (c 1.0, CH$_3$OH).

m.p.: 238–240° C.

UV: $\lambda^{CH_3OH}_{max}$ 284 nm ($\epsilon$9000), 227 nm ($\epsilon$8700).

IR: $\nu^{KBr}_{max}$ 1725cm$^{-1}$ (ester, aldehyde), 1675cm$^{-1}$ (conjugated ketone), 1590cm$^{-1}$ (double bond).

$^1$H-NMR (CDCl$_3$)'$\delta$(ppm): 1.77(3H, s, 12-CH$_3$), 2.46 (6H, s, N(CH$_3$)$_2$), 3.44 (3H, s, 2'''—OCH$_3$), 3.58(3H, S, 3'''—OCH$_3$),

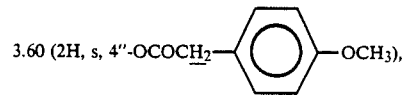

3.60 (2H, s, 4''-OCOCH$_2$—⟨⟩—OCH$_3$),

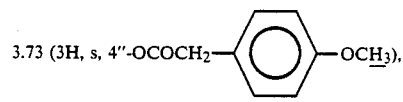

3.73 (3H, s, 4''-OCOCH$_2$—⟨⟩—OCH$_3$), 6.18 (1H, d, J=16.0 Hz, H-10),

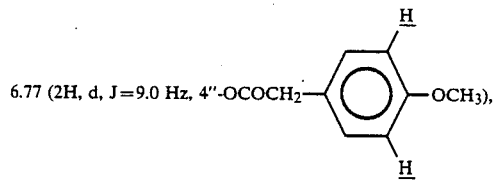

6.77 (2H, d, J=9.0 Hz, 4''-OCOCH$_2$—⟨⟩—OCH$_3$),

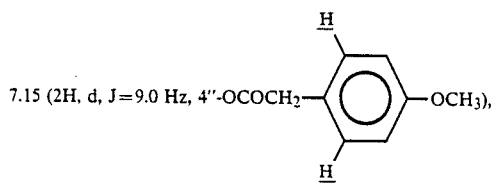

7.15 (2H, d, J=9.0 Hz, 4''-OCOCH$_2$—⟨⟩—OCH$_3$), 7.25 (1H, d, J=16.0 HZ, H-11), 9.59 (1H, s, CHO)

What is claimed is:

1. Tylosin derivatives represented by the following formula:

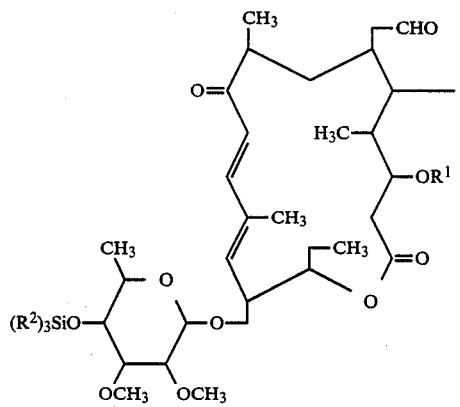

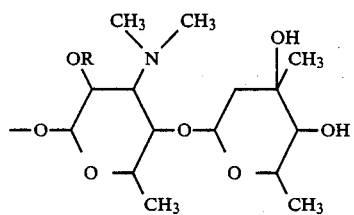

wherein R denotes a hydrogen atom, acetyl, propionyl or a radical of —Si(R$^2$)$_3$ in which R$^2$ is a lower alkyl group, and R$^1$ stands for a hydrogen atom or a radical of —Si(R$^2$)$_3$.

2. A process for producing a compound represented by the following formula IV:

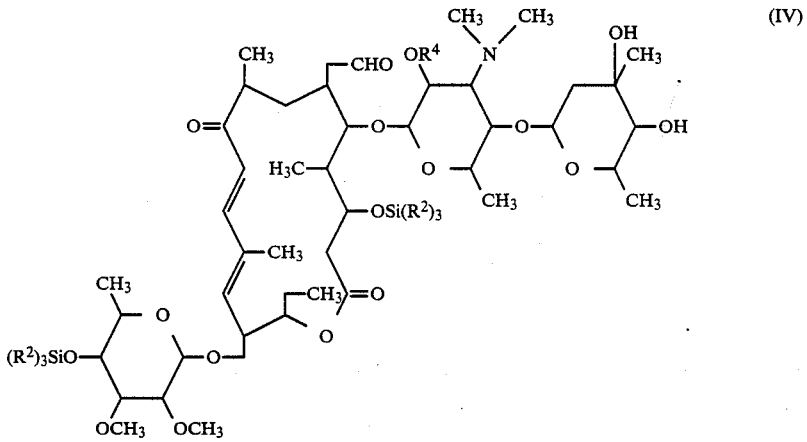

(IV)

wherein R$_4$ is acetyl, propionyl or a radical of Si(R$_2$)$_3$; and R$_2$ is a lower alkyl group, which comprises reacting a starting material selected from the group consisting of tylosin, 2'-O-acetyltylosin and 2'-O-piopionyltylosin with 0.8 to 1 mole of a boric acid compound selected from the group consisting of boric acid, boric acid anhydride, phenylboric acid or a triester of boric acid based on 1 mole of the starting material in a solvent selected from the group consisting of an aromatic hydrocarbon, a halogenated hydrocarbon, an ether, an ester, dimethylformamide, acetonitrile, dimethyl sulfoxide, a mixture of toluene-dimethyl sulfoxide, and a mixture of ethyl acetate and dimethylformamide, at a temperature of 0 to 50° C. for 0.5 to 3 hours to form a reaction mixture, followed by reacting the reaction mixture with 3 to 8 moles of a trialkylsilylating agent based on 1 mole of the starting material.

3. A process according to claim 2, wherein said aromatic hydrocarbon is selected from the group consisting of benzene and toluene.

4. A process according to claim 2, wherein said halogenated hydrocarbon is selected from the group consisting of dichloromethane, dichloroethane and chloroform.

5. A process according to claim 2, wherein said ether is selected from the group consisting of diethyl ether, tetrahydrofuran and dioxane.

6. A process according to claim 2, wherein said ester is selected from the group consisting of ethyl acetate and butyl acetate.

7. A process according to claim 2, wherein said trialkylsilylating agent is selected :rom the group consisting of trimethylchlorosilane, trimethylbromosilane, triethylchlorosilane and tripropylchlorosilane.

* * * * *